United States Patent [19]

DeProspero

[11] Patent Number: 4,719,906

[45] Date of Patent: Jan. 19, 1988

[54] UNIVERSAL ARTICULATED SPLINT

[76] Inventor: Rose DeProspero, Rte. 2, Box 79, Ireland, W. Va. 26376

[21] Appl. No.: 46,756

[22] Filed: May 7, 1987

[51] Int. Cl.⁴ ............................................... A61F 5/04
[52] U.S. Cl. ................................... 128/87 A; 128/77; 128/89 R
[58] Field of Search ..................... 128/77, 87 A, 87 R, 128/89 R, 165

[56] References Cited

U.S. PATENT DOCUMENTS

| | | | |
|---|---|---|---|
| 1,174,887 | 3/1916 | Meriwether | 128/77 |
| 1,220,476 | 3/1917 | Vjdur | 128/87 A |
| 1,232,899 | 7/1917 | DePuy | 128/89 R |
| 1,708,757 | 4/1929 | Freileweh | 128/89 R |
| 1,817,212 | 8/1931 | Siebrandt | 128/87 A |
| 2,553,277 | 5/1951 | Robinson | 128/87 A |
| 2,646,794 | 7/1953 | Baer | 128/87 A |
| 3,938,509 | 2/1976 | Barber | 128/89 R |
| 4,167,044 | 9/1979 | Girard | 128/77 |
| 4,602,620 | 7/1986 | Marx | 128/77 |

Primary Examiner—C. Fred Rosenbaum
Assistant Examiner—C. W. Shedd
Attorney, Agent, or Firm—Jones, Tullar & Cooper

[57] ABSTRACT

A hand splint with mechanism for securing it to a patient's forearm, and including a palmar hand support and plural articulated finger supports to support and immobilize each finger and the thumb independently of each other. A connection is provided between the portion of the hand splint which secures the forearm and the portion which supports the hand, to allow a variable rotation at the wrist joint which can be locked to maintain the position. Similar connections permit a locked degree of variable flexion or extension for each individual finger and thumb. Each finger support includes a plurality of finger guides assembled in sequence with the most proximal being rigidly secured to the hand support. The finger guides include articulating connections, supports for the finger or thumb, and securing bands. Individual articulated connections allow variable degrees of movement which can then be locked into desired position.

10 Claims, 7 Drawing Figures

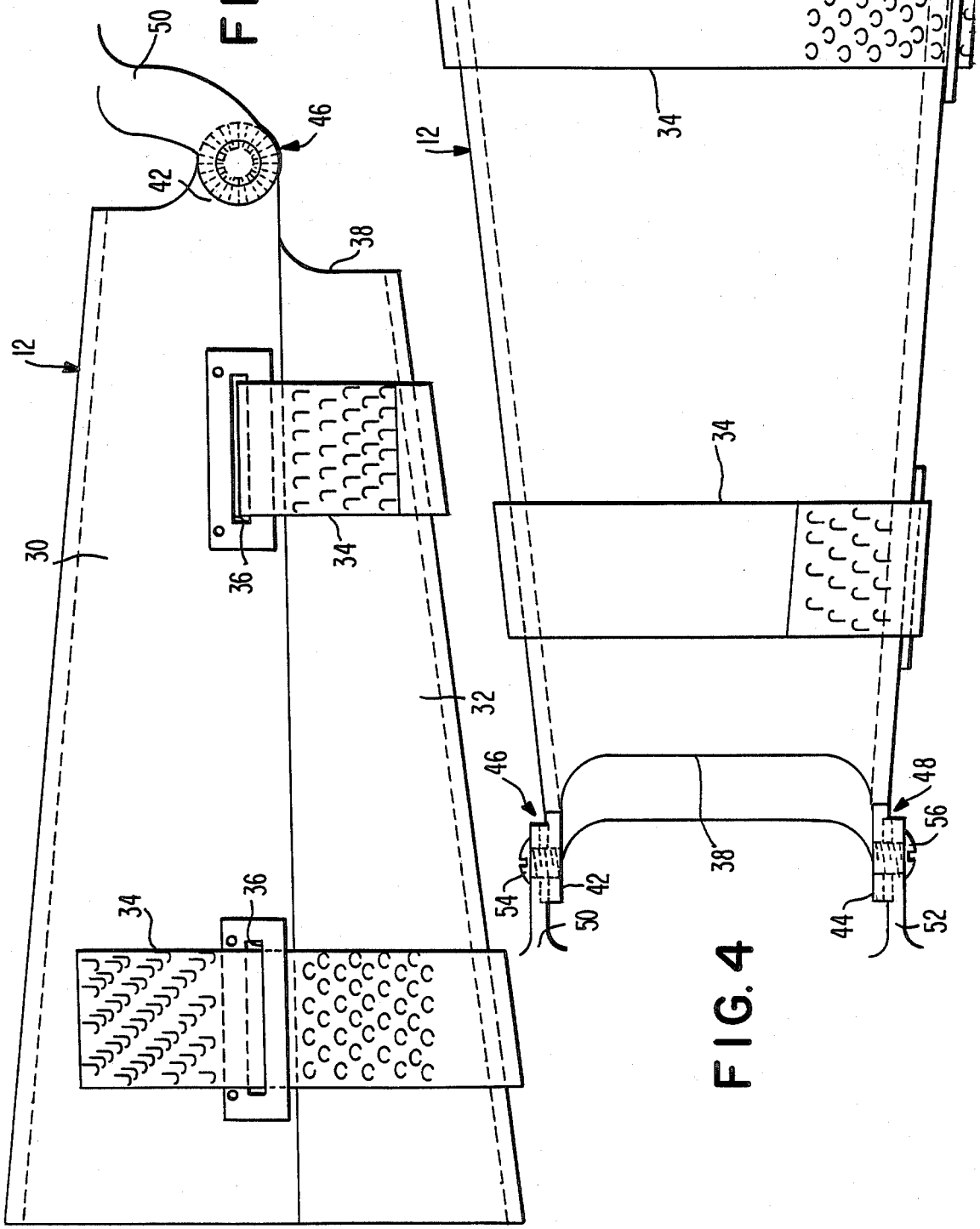

U.S. Patent    Jan. 19, 1988    Sheet 4 of 4    4,719,906
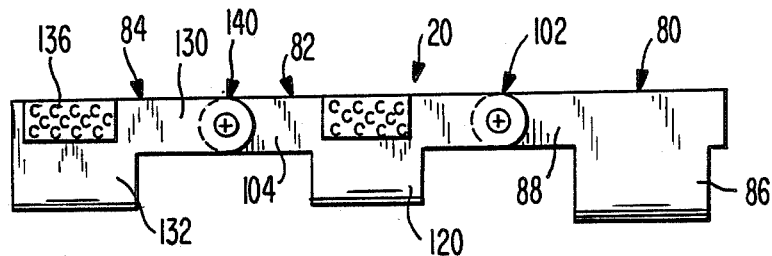
FIG. 5
FIG. 6
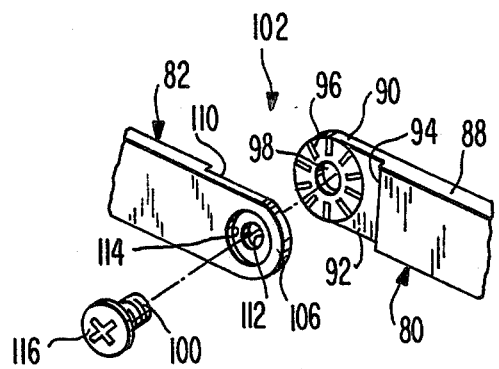
FIG. 7

UNIVERSAL ARTICULATED SPLINT

BACKGROUND OF THE INVENTION

The present invention relates, in general, to an orthopaedic splint, and more particularly to a hand splint including adjustable and lockable articulated finger and wrist joints.

Hand braces have been widely used in the treatment or support of the temporarily or permanently incapacitated hand, whether partially or fully impaired. Currently available splints or braces are basically of two types: Static or Dynamic. Static Splints traditionally have been used for positioning, whether due to the increased incidence of trauma through movement, i.e., fractures, or to try to prevent contractures and deformity through immobilization in a specific position. These devices are not oriented to producing a functionally opening hand through active exercise, nor are they particularly suited to the spastic hand which may or may not be deformed through muscle imbalances. Dynamic splints have been used to encourage exercise for weakened muscles or to supplement the use of weakened muscles in the performance of various tasks. Although these allow movement in order to strengthen or to provide technical assistance to weakened muscles, these are not suitable for the advanced development of the spastic, non-functional hand. Through the methods used, i.e., rubber bands, springs, wires or other such soft resistive methods, dynamic splints allow movement of the hand in various ways based on the assumption that the individual has some movements available and is able to perform the movement required, but needs to strengthen the muscles responsible, or that some muscles are available to "assist," through natural hand movements, other non-functioning muscles in the performance of a specific task.

SUMMARY OF THE INVENTION

An object of this invention is to provide an orthopaedic splint for the hand with connectors to control the amount of joint rotation at the wrist and individual joints of the fingers and thumb, and to be able to lock these connectors for the purpose of static positioning and/or for active exercise.

To facilitate the understanding of the hand splint and the functions it performs, the following terms need to be clarified. The forearm is that portion of the human arm from the elbow to the wrist consisting of the radius and ulna bones. The only motions that it is capable of is supination (turning the hand palm up) and pronation (turning the palm down). The wrist is the articulating joint consisting of the carpal bones between the hand and forearm. The muscles that cross the wrist joint are responsible for the relative movements of the wrist, which movements consist of extension (up), flexion (down), radial deviation (toward the thumb) and ulnar deviation (toward the little finger). The hand is comprised of the metacarpal bones and has a palmar surface and a dorsal surface. The fingers are comprised of three phalanges each, which are described as proximal (first to second knuckle joints), middle (second to third knuckle joints), and distal (third knuckle to fingertip). The first knuckle or finger joint is defined as the MP joint (metacarpal phalangeal joint). The second knuckle is the PIP joint (proximal inter-phalangeal joint), and the third knuckle is the DIP (distal inter-phalangeal joint). These joints are capable of flexion (bending) and extension (straightening) movements. The MP joints also allow the fingers to spread apart (abduction) and to come back together (adduction). A combination of these four movements is called circumduction.

The thumb is comprised of only two bones, the proximal and distal. As such, the knuckles are called the MP and DIP, respectively. Due to its position and structure, it has the basic movements described for the fingers, and in addition, also has opposition, which is a combination of flexion and adduction which enables the thumb to touch any of the finger tips. This is important, as the position of the thumb in the present invention will be held in slight extension and abduction so that the patient may actively exercise the muscles responsible for opposition.

The term range of motion effectively describes the complete movements allowed by the structural combinations at each joint.

In the broadest aspect, the present invention provides a hand splint which includes a brace securable to the forearm of a patient, and support members for the support of the patient's hand and fingers. Through an articulated joint, the hand support may be positioned in an up or down position relative to the forearm. Securing members are provided on the hand support to attach proximal finger support pieces to the hand support. Through articulating joints, middle and distal finger support pieces are assembled for each finger and thumb. The hand support is moulded to the palm of the hand and extends to the middle of the proximal phalange, or portion of the fingers and thumb. There is slight flexion moulded into the hand support to preserve flexion of the metacarpal/phalangeal joints (MP joints). The securing members form an extension of the moulded hand support to allow individual flexion at the MP joints and provide a base for the securement of the proximal finger pieces with their atticulated joint connectors and attached support bands for the fingers. In addition, securing bands are provided for securing the hand, thumb and fingers within the splint to prevent unwanted movement.

The hand splint of the present invention allows for isometric exercise through the act of trying to close the fist while the splint maintains an open hand, thereby facilitating the extensors through co-contraction across the individual joints, rather than isotonic exercise, which would allow the hand to close, thus facilitating the spasticity of the flexors and requiring the need for springs, wires, etc. to return the hand to an open position. With the addition of individual articulated finger supports, adjustments may be made: (1) to accommodate the patient's own limited range of motion at first; (2) to gradually increase the patient's range of motion over time; (3) to allow the patient to exercise aggressively on his own time by facilitating the extensors through co-contraction; and (4) to maintain control over the spastic flexors so that they cannot override the weaker extensors.

Thus, the splint of the present invention is designed to incorporate both Static and Dynamic features specifically to facilitate the spastic hand which may or may not be functionally deformed due to the spasticity. It makes allowances for the hand already contracted through spasticity by the inclusion of 9 articulated joints for the fingers, or digits, and one for the wrist. This allows a more individual fit for the initial positioning and the most beneficial positioning for the strengthening exercises themselves.

Through the use of articulating joints at the wrist and at 9 digital joints, the splint of the present invention becomes not only a positioning device to stretch contractures and maintain Range of Motion (ROM), but it also facilitates and strengthens the flexors and extensors of the fingers combined with therapy sessions. Although some splints are designed for the "normal functioning" hand which allow active exercise in order to strengthen the weakened hand, these are not suitable for the spastic hand. The articulated joints of the invention, once set by the therapist, become rigid and provide resistance to isometric exercise throughout any of the joint range of motions selected by the therapist or by the limitations of the hand itself. This results in what is known as "co-contracture" across the joints, with the usually stronger spastic flexors literally "driving" the extensors rather than allowing fist closure. This results in a more controlled resisted exercise of both components without the side effects produced by the softer materials of so-called dynamic splints, which encourage the spasticity of the flexors, thereby resulting in a tightly closed hand which cannot open. The use of the present device may extend from the hand which has no functional movement to the hand which has the ability to actively open and close within a limited ROM. Most hand splints have traditionally ignored this area of splinting due to lack of knowledge in the field and the difficulty in treating such disabilities within the feasibility of economics. The present invention is expected to provide new treatment options for Cerebral Palsy, CVA's and Head Injury patients who have lost hand function due to spasticity.

BRIEF DESCRIPTION OF THE DRAWINGS

The foregoing, and additional objects, features and advantages of the present invention, will become apparent to those of skill in the art from the following detailed description of a preferred embodiment thereof, taken in conjunction with the accompanying drawings, in which:

FIG. 3 is a side view of a forearm support showing the connection to the palmar hand support;

FIG. 4 is a top view of the forearm support of FIG. 3;

FIG. 5 is a side elevational view of a finger support used in the hand splint of FIG. 2;

FIG. 6 is a perspective view of the finger support of FIG. 5; and

FIG. 7 is a partial exploded view of the device of FIG. 6 showing an articulating connection.

DESCRIPTION OF THE PREFERRED EMBODIMENT

Figure 1:
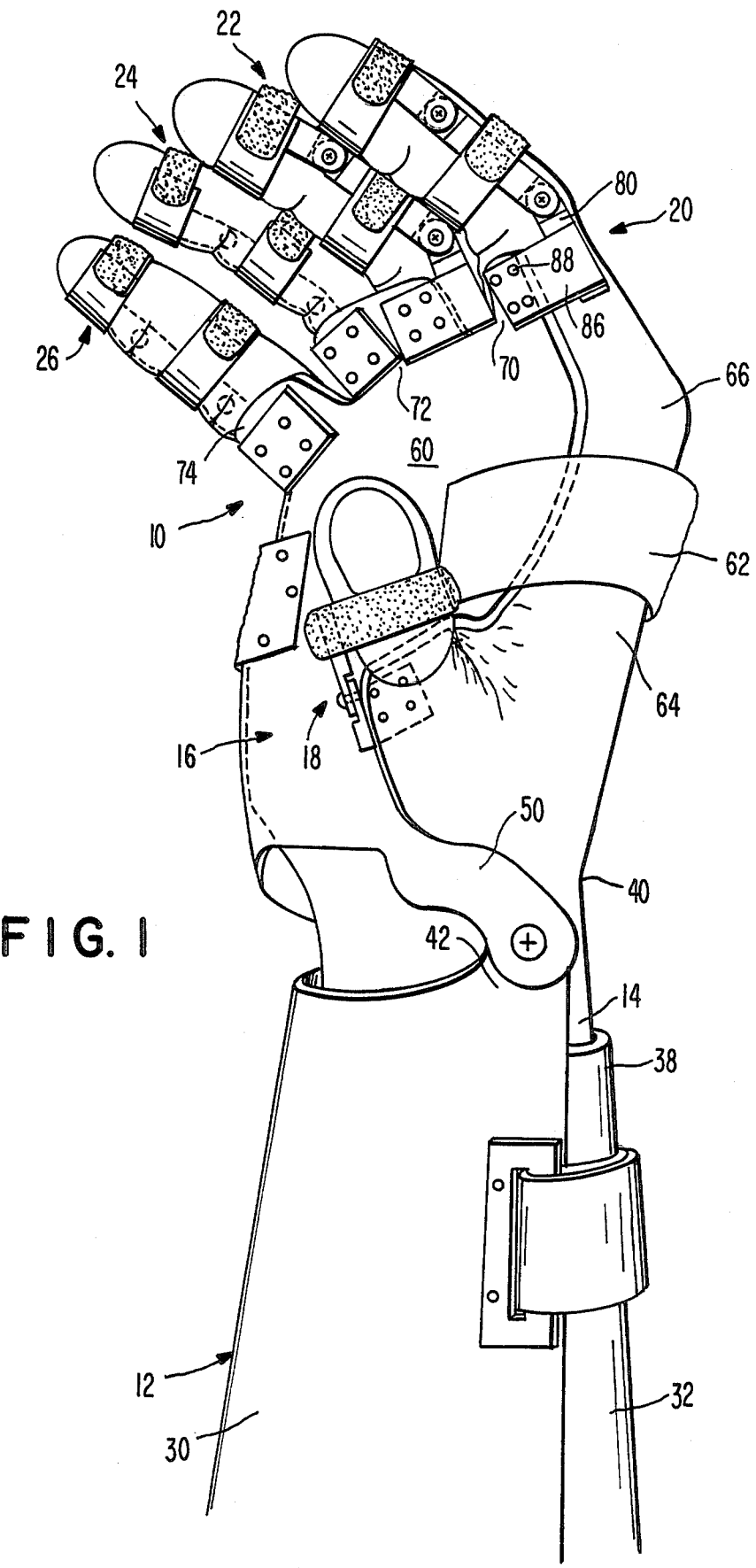
FIG. 1 is a perspective view of the hand splint constructed in accordance with the present invention, showing the articulated phalangeal and wrist supports adjusted to a functional hand position, located on a hand and connected to a forearm support.

Referring now to FIG. 1 of the present invention, a hand splint constructed in accordance with a first, simplified embodiment of the invention, as illustrated at 10. Splint 10 is comprised basically of three parts: a securing member 12 for attaching the splint to the forearm 14 of a user, a palmar hand support 16, and a plurality of finger supports generally indicated at 18, 20, 22, 24 and 26.

The forearm securing member 12 of the splint is a standard "clamshell" design with a bottom portion 30 and a top portion 32. (See FIGS. 3 and 4). Fasteners such as conventional "hook and loop" webs 34 of the type sold under the name "Velcro" are attached to the top portion 32 and pass through corresponding plastic loops 36 which are riveted to bottom clamshell 30. The straps fold over to the top portion and secure to themselves, thereby securing the two portions of the clamshell together to hold the securing member 12 in place.

The top portion 32 of the clamshell 12 is cut slightly shorter than the bottom portion at the wrist area 38 to allow for a full range of motion without the wrist 40 of the user impinging against the splint. The bottom portion 30 has a pair of extensions 42 and 44 to allow for articulating connections 46 and 48 at the wrist.

The articulating connections, or joints, 46 and 48 include a pair of extensions 50 and 52 formed on the proximal end of the palmar hand support 16. These extensions 50 and 52 curve around the hand and under the thumb area, as shown in FIG. 1, and extend to meet the corresponding extensions 42 and 44 on the forearm securing member 12. The extensions 42 and 50 are secured together by a screw 54 or other suitable fastener; similarly, the extensions 44 and 52 are secured together by a screw 56 or other suitable fastener. The screws 54 and 56 provide pivotal, or articulating, joints 46 and 48 between the palmar support 16 and the forearm securing member 12. The facing surfaces of extensions 42, 50 and extensions 44, 52 preferably are serrated or otherwise roughened so that the fasteners 54 and 56 can be tightened to lock the joints 46 and 48 to prevent relative motion between member 12 and support 16. This allows the articulating connections 46 and 48 to be adjusted to a desired angle and fixed at that angle.

Figure 2:
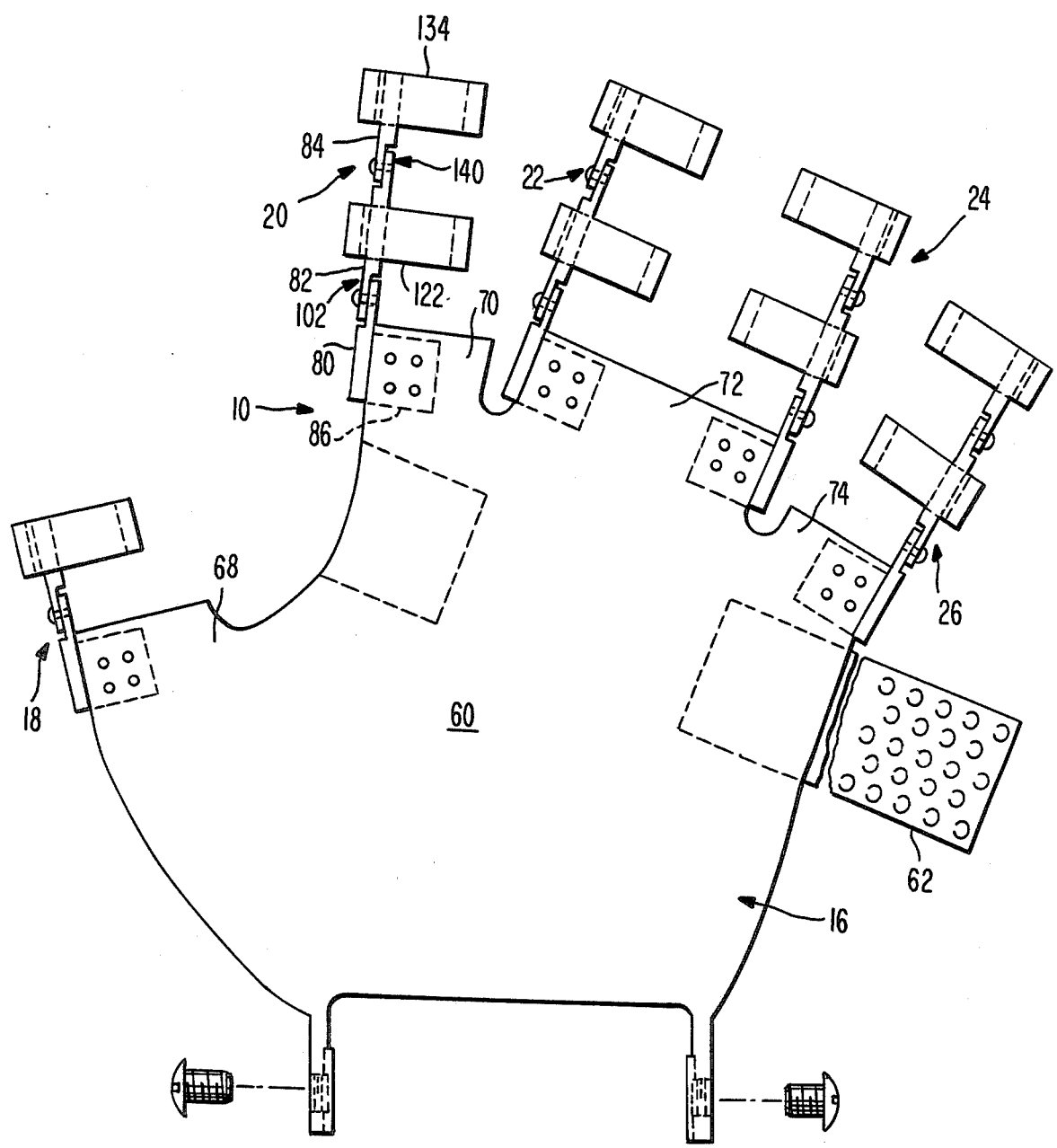
FIG. 2 is a back view of the hand splint of FIG. 1, as viewed from the right-hand side of FIG. 1, and showing the connection and securement of the phalangeal and wrist articulations of the preferred embodiment of the present invention.

The articulating connections 46 and 48 at the wrist provide a secure mounting for the palmar hand support 16. This hand support 16 is comprised of a plastic palmar portion 60 and a fastener web 62 for securing it to the hand 64 of a user. The support 16 includes the extensions 50 and 52 which provide the articulated connection to the forearm securing member 12, as described above. The palmer support 16 is moulded, preferably of plastic, to fit the individual's hand and extends beyond the MP joints, generally indicated at 66 in FIG. 1, to form base portions 68, 70, 72 and 74 for securement of the finger supports 18, 20, 22, 24 and 26, as best illustrated in FIG. 2. Also, the extended portions are slightly flexed under the MP joints to preserve flexion at these joints during exercises.

The finger supports 20, 22, 24 and 26 each consist of three parts, or phalangeal supports, which are identified by the same terms as the phalangeal components of the finger which they support. Thus, each finger support includes a proximal piece 80, a middle piece 82, and a distal piece 84 (see FIGS. 5 and 6). The proximal piece 80 of finger support 20 includes a connector tab 86 which is secured to the palmar piece 16 at extension 70, by suitable fasteners such as rivets 88. Proximal piece 80 extends to the outside of the finger and curves upwardly, where it forms a longitudinal finger guide 88 which extends along the proximal phalange of the finger to the region of the PIP joint, where it terminates in a reduced thickness joint portion 90. This joint portion includes an inner face region 92 defined by a shoulder 94, and the inner face is scored, serrated, or otherwise roughened, as illustrated by serrations 96 radially extending from near a threaded aperture 98. The threaded aperture receives a screw 100 which forms the pivot axis for an articulating joint 102 between the proximal piece 80 and the next adjacent middle piece 82 of the finger support 20.

The middle piece 82 of the finger support 20 consists of a longitudinal finger guide 104 with a reduced-thickness joint portion 106 at its proximal end and a reduced-thickness joint portion 108 at its distal end. The joint portion 106 includes a face portion 110 which is serrated in the manner illustrated for face portion 92 and which incorporates a through aperture 112 which receives screw 100. A recess 114 may be provided for the head 116 of the screw. The joint portions 90 and 106 cooperate with screw 100 to form the articulating joint, or connection, 102, the serrations on the faces of the joint portions allowing the joint to be secured at any desired angle upon tightening of the screw 100. The joint portion 108 is similar to joint portion 90 of proximal piece 80. In addition, the middle piece 82 incorporates a depending phalangeal support band 120 which wraps downwardly under the middle phalange of the finger and carries a securing member such as a web 122 of conventional hook-type fastener material which is attached to the free end of support band 120 and passes over the finger for connection to a piece 124 of loop-type fastener material secured to the middle piece 82.

The distal piece 84 consists of a longitudinal finger guide 130 with a depending support band 182 which curves downwardly and across under the distal phalange of the finger, and further includes a securing member such as a web 134 of hook-type material which passes over the finger and attaches to a piece 136 of loop fastener material. The finger guide 180 has at its proximal end a reduced-thickness joint portion 138 similar to the joint portion 106 which cooperates with joint portion 108 to form an articulating connection 140 secured by screw 142. The distal piece 84 terminates at its distal end in the support band 132.

In the preferred form of the invention, the articulating joints 102 and 140 include articulating surfaces which face each other and which are fixed by corresponding screws 100 and 142. When the screws are backed out, the matched faces of the joints move apart, allowing the joints to be rotated to the desired relative positions, and then fixed by threading the screw back into the joint.

The finger supports 22, 24 and 26 are similar to the support 20 shown in FIGS. 5-7, although for convenience in adjustment the finger guides for supports 24 and 26 are located on the opposite sides of their corresponding fingers than are the supports 20 and 22. The thumb support 18 is also similar to finger support 20, but does not incorporate the middle piece 82, since it is not required.

The finger supports 18, 20, 22, 24 and 26 preferably are formed of a strong material such as stainless steel, although a strong plastic material might be suitable for some applications. The articulating supports must be small enough so as not to impede hand function, yet strong enough to prevent failure as hand function and strength increases with exercise. The securing webs of hook and loop material allow adjustment of the device on the patient's hand and fingers, and secure the device in place.

The present invention is applied by placing the forearm, hand and phalanges in their respective supports and securing them comfortably. Final adjustments may be made at this time if necessary to accommodate the individual's joint range of motion if contractures exist. Once secured, the splint immobilizes the hand and wrist in the desired position. As additional range of motion is gained by the patient, the splint can be readjusted to include the gain. Of note here is that either flexion or extension contractures can be controlled with the use of the present invention. Contractures of varying degrees can be controlled individually without delaying advancement in other areas.

After the splint has been secured to the patient, the individual joints are set to provide a comfortable midposition for the fingers, neither totally flexed or extended, but in a "functional hand position". The therapist then instructs the patient to try to close his hand by making a fist. Other facilitation methods may be used until trace flexion appears. Once the patient has finger flexion, the splint offers resistance not only to the flexors, but to the extensors as they co-contract to stabilize the joints. By not ever allowing the flexors to make a fist, the extensors develop, never to be totally overridden by the stronger flexors. The stronger the grip, the stronger the co-contraction, and the stronger the extensors when the splint finally comes off. A patient who has had trouble opening his hand may well find that he is now able to do so and should be able to open his fingers for more theraputic exercises to increase the functional use of his hand. This splint will be beneficial to patients who have Cerebral Palsy, Head Injury or Cerebral Vascular Accidents which result in a spastic non-functional, difficult to treat hand.

Once the patient can actively open his own fingers and thumb, the splint may be reduced gradually to encourage more active exercise until the hand is functioning without the splint. This can be accomplished by removing the individual phalangeal supports at their connecting joints until the palmar support and forearm support are only providing wrist stabilization. The splint need be applied to the individual only until the desired effects have been achieved, at which point, occasional wearings may be required either to maintain the joint range of motion in cases of severe spasticity, or to continue maintenance of the strengthening exercises.

What is claimed is:

1. A hand splint comprising:
    a palmar hand support for receiving and supporting the hand of a patient;
    a plurality of finger supports for receiving and supporting the individual fingers of a patient, each said finger support including;
    (a) a proximal piece including a connector tab for rigid connection to said palmar hand support and a first longitudinally extending finger guide, said proximal piece being shaped to receive the proximal phalange of a patient's finger;
    (b) a middle piece including a second longitudinal finger guide and a first depending phalangeal support band shaped to receive and support the middle phalange of a patient's finger; and
    (c) a distal piece including a third longitudinal finger guide and a second depending phalangeal support band shaped to receive and support the distal phalange of a patient's finger;

(d) wherein said proximal piece is joined to said middle piece by a first adjustable, locking, articulating joint and wherein said middle piece is joined to said distal piece by a second adjustable, locking articulating joint, each said joint including adjustment means for locking the joint in a selectable fixed position and for releasing the joint to permit selection of a different fixed position as required by the needs of the patient; and securing means for holding the patient's hand and fingers in place in said hand splint.

2. The hand splint of claim 1, wherein each said articulating joint includes corresponding joint portions on adjacent finger guides, each joint portion including a face portion carrying locking means adapted to engage corresponding locking means on an adjacent face portion, and an adjustment means for pressing the locking means on adjacent faces together to prevent relative angular motion between adjacent finger guides.

3. The hand splint of claim 2, wherein said locking means comprises serrations on said adjacent faces.

4. The hand splint of claim 2, wherein said longitudinal finger guides are rigid and are rigidly connectable to adjacent finger guides in a finger support at selected angles determined by the position of said first and second articulating joints.

5. The hand splint of claim 1, wherein said securing means comprises webs connected to said phalangeal support bands for securing a patient's fingers in said support bands.

6. The hand splint of claim 5, wherein said securing means further includes a web connected to said palmar hand support for securing a patient's hand to said palmar hand support.

7. The hand splint of claim 1, wherein said palmar hand support is molded to fit the shape of a patient's hand, and wherein said palmar hand support further includes extensions to which said finger supports are rigidly connected.

8. The hand support of claim 7, further including forearm support means for receiving a patient's forearm, and adjustable, articulating, locking joint means for connecting said palmar support to said forearm support means to form an articulating joint in the region of a patient's wrist.

9. The hand support of claim 1, further including a thumb support for receiving and supporting the thumb of a patient, said thumb support including a proximal thumb piece connected to said palmar hand support, a distal thumb piece, and an adjustable, articulating, locking joint means connecting said distal thumb piece to said proximal thumb piece.

10. The hand support of claim 9, wherein said palmar hand support includes an extension for receiving said thumb support.

* * * * *